United States Patent
Lozano-Dubernard et al.

(10) Patent No.: US 10,201,602 B2
(45) Date of Patent: Feb. 12, 2019

(54) RECOMBINANT VACCINE AGAINST PRRS IN A VIRAL VECTOR

(75) Inventors: Bernardo Lozano-Dubernard, Mexico City (MX); Ernesto Soto-Priante, Mexico City (MX); David Sarfati-Mizrahi, Mexico City (MX); Jesús Horacio Lara-Puente, Mexico City (MX)

(73) Assignee: LABORATORIO AVI-MEX, S.A. DE C.V., Del. Iztapalapa (MX)

( * ) Notice: Subject to any disclaimer, the term of this patent is extended or adjusted under 35 U.S.C. 154(b) by 305 days.

(21) Appl. No.: 14/116,319

(22) PCT Filed: May 7, 2011

(86) PCT No.: PCT/IB2011/000977
§ 371 (c)(1),
(2), (4) Date: Mar. 11, 2014

(87) PCT Pub. No.: WO2012/153160
PCT Pub. Date: Nov. 15, 2012

(65) Prior Publication Data
US 2014/0199343 A1  Jul. 17, 2014

(51) Int. Cl.
*A61K 39/12* (2006.01)
*C12N 7/00* (2006.01)
(Continued)

(52) U.S. Cl.
CPC .............. *A61K 39/17* (2013.01); *A61K 39/12* (2013.01); *C12N 15/86* (2013.01);
(Continued)

(58) Field of Classification Search
None
See application file for complete search history.

(56) References Cited

U.S. PATENT DOCUMENTS

| 5,888,513 A | 3/1999 | Plana et al. |
| 5,998,601 A | 12/1999 | Murtaugh et al. |

(Continued)

FOREIGN PATENT DOCUMENTS

| CN | 1554766 A | 12/2004 |
| WO | 2007040876 A2 | 4/2007 |
| WO | 2010058236 A1 | 5/2010 |

OTHER PUBLICATIONS

Kim et al., "Biological and Phylogenetic Characterization of Pigeon Paramyxovirus Serotype 1 Circulating in Wild North American Pigeons and Doves," Journal of Clinical Microbiology vol. 46, No. 10: 3303-3310 (2008).*

(Continued)

*Primary Examiner* — Janet L Andres
*Assistant Examiner* — M Franco G Salvoza
(74) *Attorney, Agent, or Firm* — Browdy and Neimark, P.L.L.C.

(57) ABSTRACT

A live or inactivated recombinant vaccine is described, comprising a viral vector and a pharmaceutically acceptable vehicle, adjuvant and/or excipient, wherein the viral vector is capable of generating a cell immune response due to an increased alpha and/or gamma interferon production, and is capable of a quick replication, and it has inserted a nucleotide sequence of the ORF 5 and ORF 6 from PRSS.

14 Claims, 2 Drawing Sheets

Specification includes a Sequence Listing.

(51) Int. Cl.
  *A61K 39/17* (2006.01)
  *C12N 15/86* (2006.01)
  *A61K 39/00* (2006.01)
(52) U.S. Cl.
  CPC ............... *A61K 2039/5252* (2013.01); *A61K 2039/5254* (2013.01); *A61K 2039/5256* (2013.01); *A61K 2039/552* (2013.01); *A61K 2039/55566* (2013.01); *A61K 2039/572* (2013.01); *C12N 2760/18041* (2013.01); *C12N 2760/18134* (2013.01); *C12N 2760/18141* (2013.01); *C12N 2770/10034* (2013.01)

(56) References Cited

U.S. PATENT DOCUMENTS

| | | | |
|---|---|---|---|
| 6,207,165 | B1 | 3/2001 | Audonnet et al. |
| 6,410,031 | B1* | 6/2002 | Kwang et al. ............ 424/218.1 |
| 7,041,443 | B2 | 5/2006 | Schmitz et al. |
| 7,442,379 | B2* | 10/2008 | Garcia-Sastre ...... C07K 14/005 424/199.1 |
| 7,722,878 | B2 | 5/2010 | Vaughn et al. |
| 2002/0155581 | A1* | 10/2002 | Murphy et al. ............ 435/235.1 |
| 2010/0330190 | A1* | 12/2010 | Compans ............ A61K 39/145 424/499 |
| 2011/0150912 | A1* | 6/2011 | Perez .................... A61K 39/145 424/186.1 |
| 2011/0162115 | A1* | 6/2011 | Guo ..................... A61K 39/17 800/301 |
| 2012/0276139 | A1* | 11/2012 | Moormann ............ A61K 39/17 424/199.1 |

OTHER PUBLICATIONS

Samal et al., "A single amino acid change, Q114R, in the cleavage-site sequence of Newcastle disease virus fusion protein attenuated viral replication and pathogenicity," Journal of General Virology, 92: 2333-2338 (2011).*

Miller et al., "Newcastle disease: Evolution of genotypes and the related diagnostic challenges," Infection, Genetics and Evolution 10: 26-35 (2010).*

Olav S. de Leeuw et al., "Effect of fusion protein cleavage site mutations on virulence of Newcastle disease virus: non-virulent cleavage site mutants revert to virulence after one passage in chicken brain", Journal of General Virology, pp. 745-484, (2003).

Takaaki Nakaya et al. "Recombinant Newcastle Disease Virus as a Vaccine Vector", Journal of Virology, pp. 11868-11873, vol. 75, No. 23, (2001).

Yunbo Jiang et al., "DNA vaccines co-expressing GP5 and M proteins of porcine reproductive and respiratory syndrome virus (PRRSV) display enhanced immunogenicity", Vaccine, pp. 2869-2879, vol 24., (2005).

Qisheng Zheng et al., Co-expressing GP5 and M proteins under different promoters in recombinant modified vaccinia virus ankara (rMVA)-based vaccine vector enhanced the humoral and cellular immune responses of porcine reproductive and respiratory syndrome virus (PRRSV), Virus Genes, pp. 585-595, vol. 35, (2007).

Joshua M. DiNapoli et al., "Newcastle disease Virus, a host range-restricted virus, as a vaccine vector for intranasal immunization against emerging pathogens" PNAS, pp. 9788-9793, vol. 104, No. 23, (2007).

Jinshun Cai et al., "Construction and Characterization of a Recombinant Canine Adenovirus Expressing GP5 and M proteins of Porcine Reproductive and Respiratory Syndrome Virus", J. Vet. Med. Sci., pp. 1035-1040, vol. 72, No. 8, (2010).

Dinapoli, et al., Newcastle Disease Virus-Vectored Vaccines Expressing the Hemagglutinin or Neuraminidase Protein of H5N1 Highly Pathogenic Avian Influenza Virus Protect against Virus Challenge in Monkeys, Journal of Virology, Feb. 2010, pp. 1489-1503, vol. 84, No. 3.

Lozano-Dubernard, et al., Protection and Differentiation of Infected from Vaccinated Animals by an Inactivated Recombinant Newcastle Disease Virus/Avian Influenza H5 Vaccine, Avian Diseases, 2010, pp. 242-245, vol. 54.

Sarfati-Mizrahi, et al., Protective Dose of a Recombinant Newcastle Disease LaSota-Avian Influenza Virus H5 Vaccine Against H5N2 Highly Pathogenic Avian Influenza Virus and Velogenic Viscerotropic Newcastle Disease Virus in Broilers and High Maternal Antibody Levels, Avian Diseases, 2010, pp. 239-241, vol. 54.

* cited by examiner

RECOMBINANT VACCINE AGAINST PRRS IN A VIRAL VECTOR

FIELD OF THE INVENTION

The present invention is related to the techniques used in the prevention and control of Porcine Reproductive and Respiratory Syndrome (PRRS), and more particularly, it is related to a viral vector recombinant vaccine having inserted an exogenous nucleotide sequence coding for proteins with antigenic activity against the PRRS virus, and a pharmaceutically acceptable vehicle, adjuvant and/or excipient.

BACKGROUND OF THE INVENTION

The Porcine Reproductive and Respiratory Syndrome virus (vPRRS) is an enveloped virus belonging to the RNA group, Arteriviridae family, *Arterivirus* genus. Its size ranges around 460 nm and its viral genome is comprised by a RNA strand in the positive sense, which results in 7 open reading frames (ORF), ORF1a, ORF1b, ORF2-ORF7, which in turn results in the assembling of 7 structural proteins (gp 2a, 2b-5, M and N) and at least 13 non-structural proteins (nsp 1a, nsp 1b-nsp 12), each one with specific functions forming the vPRRS. This virus shows an immunomodulatory behavior when selectively infects the monocyte/macrophage cell line in charge of starting the immune response and of participating in the direction of the immune response, inter alia. The virus has proven ability to alter the immune response by decreasing the gamma interferon (IFNγ) production, and the late production of neutralizing antibodies, and the production of immunological decoys (Yoo et al., 2009; Sang et al., 2009; Patel et al., 2009; Chen et al., 2009; Lalit, 2009). Since vPRRS has a high antigenic variability, it has been difficult to use the traditional method based on various vaccination strategies to combat it. Because of this, worldwide efforts are being made to develop a biological able to combat the diffusion of the infection and the effects thereof, being the genetic manipulation products of the virus the best options to achieve this (Lara, 2010). In this sense, the viral subunits which could give any kind of protection are being also studied, the use of ORF 5 and ORF 6 has shown good expectations because they are responsible, at least in part, for the virus virulence (Kim et al., 2009; Zuckerman et al., 2007), proving that immunity is achieved with live (replicating) products as these are the only ones giving protection in a challenge, this protection being measured by the decrease in post-challenge viraemia. In 2005, ORF 5 mutants were developed by modifying their glycosilation and they were tested as immunogens, finding that the GP5 hypo-glycosilation increases the ability of the vPRRS to induce in vivo neutralizing antibodies (Ansari et al., 2005).

In the specific case of ORF 5, the region between the amino acid residues 1-25 has a high variability among American and European isolates, while the hypervariable region of the strain regions in each continent is grouped between amino acids 26 and 39, near the amino acid terminal sequence.

The change in the ORF 5 sequence may result in atypical outbreaks of the disease as the swine abortion and mortality syndrome (SAMS), or the "high fever" syndrome seen in China (Ferrari et al, 2003; Martelli, 2003).

The vaccine against PRRS currently commercialized contains an attenuated virus, however, it has the disadvantage of having the possibility of infecting the pigs, resulting in disease development and immunological damage, mainly in naive animals (highly susceptible without previous exposition); additionally, it has been shown that this vaccine virus mutates and can recombine itself with the circulating field viruses, thus creating new genetic variants of the virus. Likewise, studies have been made showing that the live attenuated vaccine is not completely efficient to prevent the disease, also, previously it has been shown that the anti-vPRRS antibodies are involved in the amplification mechanism of the antibodies dependent enhancement (ADE) and/or in immunopathology caused by vPRRS (Thanawongnuwech and Suradhat, 2010), which could cause that, contrary to the expectation, the vaccinated animals become more susceptible to the effects of the PRRS disease.

Due to the above, there are several patents related to recombinant vaccines against this disease.

U.S. Pat. No. 7,722,878 discloses recombinant vaccines against PRRS, consisting of a vector comprising an ORF 1 portion of the vPRRS, alone or combined with another ORF. These vaccines are useful to induce an immune response in animals, and to prevent and decrease the condition severity and symptoms caused by a vPRRS infection. In order to determine the efficiency of these vaccines, the number of lung lesions, characteristic of vPRRS, was measured, achieving a decrease in said lung lesions up to 47%.

In U.S. Pat. No. 5,888,513, recombinant proteins corresponding to ORF2-ORF7 of a vPRRS isolated in Spain are disclosed, which are produced in a baculovirus expression system, and which can be used in vaccines formulation.

Chinese Patent Applications Nos. CN1554766A and CN1800375A describe recombinant vaccines against PRRS, which use an adenovirus as a vector. Likewise, Chinese Patent Application No. CN1778926A disclose an ORF 5 modified gene of the vPRRS, which can be used in the preparation of a vaccine against this disease.

In U.S. Pat. No. 7,041,443, virus, polynucleotides and polypeptides of the European type PRRS are described, which may be used in the preparation of immunogenic compositions, which consist in an attenuated or inactivated vPRRS including a polynucleotide selected from several sequences.

On the other hand, U.S. Pat. No. 6,207,165 discloses a multivalent vaccine formula for pig vaccination against pathogen agents involved in reproductive and/or respiratory pathologies, one of them being PRRS. The vaccine includes at least three types of vaccines, each one comprising a plasmid and a gene with a porcine pathogen valence, which in case of PRRS can be the E, ORF 3 or M genes.

Finally, U.S. Pat. No. 5,998,601 discloses VR-2332 strain nucleotide sequences of vPRRS, which can code for ORFs or fragments thereof, as well as vaccines derived thereof.

In spite of the above, although the vaccines described in the state of the art have served to attenuate the effects of the disease, up to date a level of protection against vPRRS that is sufficient for an effective disease control has not been achieved.

OBJECTS OF THE INVENTION

Having in mind the drawbacks in the prior art, an object of the present invention is to provide an effective viral vector recombinant vaccine against Porcine Reproductive and Respiratory Syndrome (PRRS).

Another object of the present invention is to provide a viral vector recombinant vaccine against PRRS, producing a quicker immune response than a vaccine based in the whole PRRS virus.

A further object of the present invention is to provide the use of a viral vector recombinant vaccine for controlling PRRS.

It is another object of the present invention, providing a viral vector construction having inserted an exogenous nucleotide sequence coding for proteins with antigenic activity against PRRS virus.

BRIEF DESCRIPTION OF THE INVENTION

To this end, a recombinant vaccine has been invented comprising a viral vector capable of generating a cellular immune response due to an increased production of alpha and/or gamma interferon, and capable of a quick replication, preferably based on the Newcastle disease virus, having inserted a nucleotide sequence of PRRS selected from ORF 5, ORF 6 and combinations thereof, and a pharmaceutically acceptable vehicle, adjuvant and/or excipient.

BRIEF DESCRIPTION OF THE DRAWINGS

The novel aspects considered characteristics of the present invention will be particularly established in the appended claims. However, some embodiments, features and some objects and advantages thereof, will be better understood in the detailed description, when read with regard to the appended drawings, wherein:

DETAILED DESCRIPTION OF THE INVENTION

Figure 1:
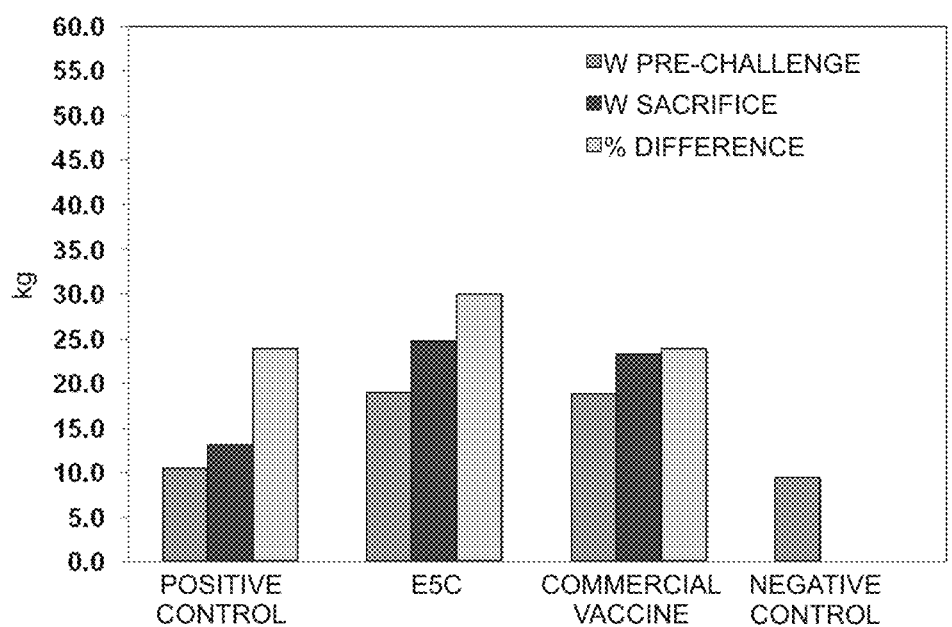
FIG. 1 shows the body weight gain in pigs immunized with the inactivated vaccines against PRRS of the present invention, compared to the commercial vaccine.

While developing the present invention, surprisingly it has been found that a recombinant vaccine comprising a viral vector capable of generating a cellular immune response due to an increased production of alpha and/or gamma interferon, and capable of a quick replication, having inserted an exogenous nucleotide sequence coding for antigenic sites of the PRRS virus (vPRRS), and a pharmaceutically acceptable vehicle, adjuvant and/or excipient, provides a suitable protection against the Porcine Reproductive and Respiratory Syndrome.

The viral vector used can be live (active) or inactivated (dead). By inactivated it is understood that the recombinant virus acting as a viral vector and having the nucleotide sequence coding for antigenic sites of vPRRS has lost the replication capability. The inactivation is achieved by physical or chemical procedures well known in the art, preferably by chemical inactivation with formaldehyde or beta-propiolactone (Office International des Epizooties 2008). Newcastle Disease. OIE Manual of Diagnostic Tests and Vaccines for Terrestrial Animals. Office International des Epizooties. France, p. 576-589). On the contrary, by active or live virus it is understood that it retains its replication capability.

Preferably, the viral vector used is a paramyxovirus, selected from any paramyxovirus, including any serotype, genotype or genetic type, including lentogenic, mesogenic and velogenic viruses. Likewise, it is possible to use paramyxovirus to which reverse genetics techniques can be carried out in order to remove the phenylalanine from the 117 position, and the basic amino acids from the position close to Q114 position, which give the pathogenicity to the paramyxovirus, or paramyxovirus included in birds-infecting *Avulavirus* genus, such as the Newcastle disease virus or the Sendai virus. More preferably, the viral vector is the Newcastle disease virus, said viral vector is selected preferably from lentogenic or mesogenic strains, such as LaSota, B1, QV4, Ulster, Roakin, Komarov strains. Preferably, the recombinant virus is from a LaSota strain.

Regarding the nucleotide sequence coding for antigenic sites of vPRRS, in the prior art several ORFs sequences have been described, as that of ORF 5 and ORF 6, which can be used to produce vaccines against PRRS, such as those disclosed in U.S. Pat. Nos. 5,885,513 and 7,041,443, and in the Chinese Patent Application No. CN1778926A. In the case of the present invention, the nucleotide sequences used are selected from those described in SEQ ID NO:1 (ORF 5), SEQ ID NO:2 (ORF 6), and combinations thereof.

The viral vector of the vaccine of the present invention can be prepared by amplifying by PCR the nucleotide sequence of interest which will be inserted then, already amplified, in the paramyxovirus viral vector. The insertion is carried out using molecular biology cloning standard techniques. The infectious clone thus obtained is transfected in a cell culture to generate the recombinant virus.

The virus replicates in any system suitable for its growing, such as SPF chicken embryo, or commercial cell lines, or cell lines expressly designed to grow the virus, until reaching the virus concentration required to achieve the antigenic response, preferably between $10^{8.0}$ and $10^{10.0}$ EID50%/mL, more preferably between $10^{8.0}$ and $10^{9.5}$ EID50%/mL. In the live vaccine embodiment, it is used a naturally lentogenic vaccine active virus, or one attenuated by procedures already known in the art. On the other hand, when the vaccine is inactivated, once reached the viral concentration required to achieve the antigenic response, the virus is inactivated. Preferably, the inactivation is made by physical or chemical procedures well known in the art, preferably by chemical inactivation with formaldehyde, beta-propiolactone or binary ethylenamine (B.E.I.).

Pharmaceutically acceptable vehicles for the vaccines of the present invention are preferably aqueous solutions or emulsions. More particularly, it is preferred that the used vehicle is a water-oil, oil-water, or water-oil-water (WOW) emulsion, preferably a water-oil-water emulsion. Regarding the vaccine administration, this can be carried out intramuscularly, intranasally, subcutaneously, by aspersion, spraying, or in drinking water, in each case using suitable means and forms for pigs, and depending if it is a live vaccine or an inactivated vaccine; preferably is administered by intramuscular or intranasal route, more preferably by intramuscular route.

The present invention will be better understood from the following examples, which are only illustrative to allow a well understanding of the preferred embodiments of the present invention, without meaning that other non-illustrated existing embodiments can be practiced based on the above detailed description.

EXAMPLES

Example 1

Production of the Newcastle LaSota Vector

In order to clone the genome of the Newcastle virus, strain LaSota, and thus generate a viral vector, firstly, an intermediate vector was created, called "pSL1180NDV/LS". To this end, total viral RNA extraction of Newcastle strain LaSota was carried out by the triazole method. From the purified RNA, the synthesis of cDNA (complementary DNA) of the viral genome was performed, using the total RNA previously purified as a template. With the purpose of cloning all the genes from the Newcastle genome (15, 183 base pairs (bp)), 7 fragments with "overlapping" ends and cohesive restriction sites were amplified by PCR. Fragment 1 (F1) covers nucleotides (nt) 1-1755, F2 goes from nt 1-3321, F3 comprises from nt 1755-6580, F4 goes from 6,151-10, 210, F5 includes from nt 7,381-11,351, F6 goes from 11,351-14, 995 and F7 comprises from nt 14,701-15,186. The assembly of the 7 fragments was made inside a cloning vector called pGEM-pSL1180 using linking standard techniques, which allowed rebuilding the Newcastle LaSota genome, which after cloning has a single restriction site SacII, between P and M genes, and which is useful for cloning any gene of interest in this vector viral region.

Example 2

Cloning of the ORF 5 and ORF 6 Genes from vPRRS

To clone the ORF 5 and ORF 6 genes from vPRRS, total viral RNA extraction was carried out by the Triazole method. This purified total RNA was then used to synthesize the cDNA (complementary DNA), and by the PCR technique, said genes from PRRS virus were amplified using specific oligonucleotides. ORF 5 and ORF 6 genes were inserted later in the fermentas pJET vector using cloning standard techniques, thus obtaining the plasmid: pJETORF5/ORF6.

Example 3

Cloning of the ORF 5 and ORF 6 Genes from vPRRS within SacII Site of pSL1180 NDV/LS Vector to Produce Plasmid pNDV-LS(wt)Orf⅚

A: Production of the pIntNhe Intermediate Vector

With the purpose of introducing the transcription sequences from Newcastle called GE/GS in the 5' end of ORF 5 and ORF 6 genes, a new intermediate vector was built, called pintNhe, by the PCR initial amplification of the GE/GS sequences, taking the Newcastle genome as a template, and the later insertion of these sequences in pGEM-T.

B: Subcloning of the ORF 5 and ORF 6 Genes to Vector pIntNhe

The pIntNhe plasmid was digested with SpeI-HpaI and then cloned into the pIntNhe, obtaining the pInt Nhe 56 plasmid.

C: Subcloning of GE/GS-ORF⅚to Vector pSL1180NDV/LS

The pINTNhe 56 plasmid was digested with NheI enzyme and the PSL1180 NDV/LS plasmid was digested with SacII; digestion products were shaved off in order to leave compatible linking sites, and the GE/GS-ORF⅚region was purified and inserted into SacII site of pNDV/LS, thus obtaining the infecting clone called pNDV-LS(wt) Orf⅚.

Example 4

Production of recombinant virus rNDV-LS(wt)Orf⅚in cell culture

Hep-2 and A-549 cells were first infected with MAV-7 virus at an infection multiplicity (MOI) of 1. After incubation for 1 hour at 37° C. in a 5% $CO_2$ atmosphere, the cells were transfected with 1 microgram (μg) of DNA from the pNDV-LS(wt) Orf⅚clone, together with 0.2 μg of DNA from the expression plasmids pNP, pP and pL, which code for the viral proteins P, NP and L, required for the production of the recombinant in both cell types. Forty four hours after transfection, the recombinant virus obtained in both cell types was harvested and injected to 10 days-old SPF chicken embryos to amplify the produced virus. The allantoid liquid harvested was titred by plate assay in Vero cells, thus generating the final recombinant virus, used for preparing the vaccines.

Example 5

Manufacturing Method of the Vaccine with Newcastle LaSota Recombinant Virus Having ORF 5 and ORF 6 Inserts from vPRRS: pNDV-LS(wt)Orf⅚vac Starting from production seeds, chicken embryonated eggs, free of specific pathogens (SPF), were inoculated with the previously determined infecting dose. The embryos were incubated at 37° C. for 72 hours, mortality being monitored daily. After this time, the living embryos were refrigerated from one day to the next day, preferably 24 hours, the aminoallantoid liquid (FAA, by its Spanish acronym) was harvested in aseptic conditions and was clarified by centrifugation. The FAA was subjected to tests to determine its purity, sterility and Embryo Infection Dose (EID) titer.

The active and inactivated vaccines were prepared in a water-oil-water type emulsion. To prepare the oily phase, mineral oil and surfactants of the Span 80 and Tween 80 type were used. To prepare the aqueous phase, the FAA was mixed with a preservative solution (thimerosal). To prepare the emulsion, the aqueous phase was slowly added to the oily phase with constant stirring. A homogenizer or colloidal mill was used to reach the specified particle size.

The above vaccines were formulated to give a minimum of $10^{8.0}$ DIEP50%/0.5 mL, in order to use a dose of 2.0 mL per pig.

According to the above-described procedure, a recombinant experimental vaccine was produced in vector (pSL1180 NDV/LS) with ORF 5 and ORF 6 genes, called pNDV-LS (wt)/Orf⅚vac, which was tested in the live form without adjuvant (Example 5A), live form with a water-oil-water adjuvant (Example 5B), and inactivated form with a water-oil-water adjuvant (Example 5C), applied in two doses in all cases.

Example 6

In Vivo Assessment of the Recombinant Vaccine pNDV-LS(wt)/Orf⅚Vac Potency

In order to determine the efficacy of the vaccines of the present invention and to demonstrate that these may be more effective than the commercial vaccine (applied in 1 dose), the efficacy thereof was tested.

A pathogen active virus of PRRS was used, at a dose of $10^{6.0}$ DICC50% mL/45 minutes, to challenge in the different experiments in order to measure the vaccines efficacy.

To this end, 104 SPF pigs, 3 to 5 weeks-old, were used, which were ear-tagged in duplicate with an individual number, weighted and randomly assigned to 9 treatment groups, according to Table 1.

TABLE 1

| | E5A (live vaccine), 2 doses | | E5B Live vaccine with adjuvant, 2 doses | | E5C Inactivated vaccine with adjuvant, 2 doses | | Negative control | Challenged non-vaccinated (positive control) | Subtotal |
|---|---|---|---|---|---|---|---|---|---|
| | Sentinels | Test | Sentinels | Test | Sentinels | Test | | | |
| Negative control | NA | NA | NA | NA | NA | NA | 10 | NA | 10 |
| pNDV-LS(wt)Orf5/6 vac | 3 | 10 | 3 | 10 | 0 | 10 | 0 | 3 | 39 |
| Ingelvac ® PRRS MLV (1 single dose) | 3 | 10 | NA | NA | NA | NA | 0 | 3 | 16 |
| Subtotal | 6 | 20 | 3 | 10 | 0 | 10 | 10 | 6 | 65 |

The pigs were housed in isolation rooms with negative pressure, and were allowed to acclimate for 3 days before treatment. For all groups, the animals were fed with commercial food, and drinking water for domestic use was supplied ad libitum; both the food and drinking water were free from additives and/or antibiotics. Likewise, air filtration systems and air seals were placed in each room. The pigs were immunized in day 0 and day 14 with the vaccines of the present invention, obtained according to Examples 5A-5C (pNDV-LS(wt)/Orf5/6vac), and using a 2.0 mL per pig dose. For comparison purposes, other group was immunized with a single 2.0 mL dose (manufacturer's suggestion) per pig with the commercial vaccine commonly used against PRRS (Ingelvac® PRRS MLV).

The vaccination day was designated as "post-vaccination day zero" (DPV 0). Likewise, blood samples were taken from the animals in all groups by puncture in the vena cava, in the following dates: DPV 0, DPV 7, DPV 14, DPV 21, DPV 28, DPV 35, DPV 42, and DPV 49 (sacrifice).

The challenge was made on DPV 35 (DPDF 0) in all pigs of all groups, except the negative control group; the challenge virus was administered by spraying in a chamber specifically designed for the pigs. On day DPV 49 or DPDF 14, all the pigs in all groups were sacrificed and subjected to post-mortem test. In order to prove the vaccine effectiveness, the growth performance and the percentage of lung lesions in the immunized pigs were assessed.

Percentage of Lung Lesions

The pigs from the different groups were sacrificed on DPDF 14, by electroshock and bleeding, followed by necropsy. The insufflated lungs, still attached to the trachea, were removed. The assessment included right and left apical lobes, right and left cardiac lobes, left cranial edge and right diaphragmatic lobe and middle lobe. Depending on the presence or absence of injuries, tissue samples were collected from the affected organs. The macroscopic injuries suggestive of infection by vPRRS (defined as areas having possible interstitial pneumonia), were determined with the planimetry method (Ciprian et al., 1988, Lara et al, 2008); the results are shown in Table 1.

TABLE 1

| Decrease in lung lesions in pigs vaccinated against PRRS | | |
|---|---|---|
| Treatment | Lung lesion % | Decrease in lung lesion % |
| Negative control | 0.07 | NA |
| E5A (pNDV-LS(wt)/Orf5/6 vac live), 2 doses | 3.92 | 67.30 |
| E5B (pNDV-LS(wt)/Orf5/6 vac live + adjuvant), 2 doses | 7.27 | 39.36 |
| E5C (pNDV-LS(wt)/Orf5/6 vac inactivated + adjuvant), 2 doses | 5.20 | 56.63 |
| Ingelvac PRRS MLV | 15.54 | −129.60 |
| Positive control | 11.99 | 0 |

As can be seen, with the administration of the vaccines pNDV-LS(wt)Orf5/6vac in its different variants (live, live with adjuvant and inactivated with adjuvant) it was possible to decrease the percentage of lung lesions up to 67%, when compared to the positive control, while the percentage of lung lesions increased in about 30% with respect to the positive control by using the commercial vaccine. This is consistent with that informed in the state of the art (Thanawongnuwech and Suradhat, 2010).

Serology

Blood samples obtained from the animals in all groups were used to make the serology tests, selecting those corresponding to the basal sampling, to the day before challenge and to the day of sacrifice. Seroconversion tests were made using ELISA Herd Check PRRS 2XR of IDEXX according to the manufacturer's instructions. The found results are shown below:

TABLE 2

| Percentage of seroconversion | | | |
|---|---|---|---|
| Treatment | Basal | Pre-challenge | Sacrifice |
| Negative control | 0% | 0% | 0% |
| E5A (pNDV-LS(wt)/Orf5/6 vac live), 2 doses | 0% | | 0% |

TABLE 2-continued Percentage of seroconversion

| Treatment | Basal | Pre-challenge | Sacrifice |
|---|---|---|---|
| E5B (pNDV-LS(wt)/Orf5/6 vac live + adjuvant), 2 doses | 0% | 0% | 0% |
| E5C (pNDV-LS(wt)/Orf5/6 vac inactivated + adjuvant), 2 doses | 0% | 0% | 0% |
| Ingelvac PRRS MLV | 0% | 80% | 100% |
| Positive control | 0% | 0% | 0% |

The above results show that, according to that expected, in the basal sampling all SPF pigs were negative. At the time of the challenge, the only group seroconverted was that immunized with the Ingelvac PRRS MLV vaccine, while no seroconversion was detected in any of the groups immunized with the vaccines of the present invention. This result is because the commercially available ELISA kit only detects antibody response against the nucleocapside protein coded by ORF 7, which is not present in any of the vaccines of Examples 5A-5C.

Regarding the time of sacrifice, it can be seen that the group vaccinated with the commercial vaccine remained seropositive and the rest of the groups seronegative, this may be due to the short time elapsed between the challenge and the sacrifice, and the time for seroconversion of the challenge virus used was not enough. However, the presence of the virus in all the challenged groups was confirmed by PCR tests.

Likewise, with the aim to detect seroconversion to the pNDV-LS(wt)Orf5/6vac in its different embodiments, and using the above-mentioned serologic samples, the HI test was run using the method already described in the state of the art. The obtained results are shown in Table 3.

TABLE 3

Percentage of seroconversion by the HI test for pNDV-LS(wt)Orf5/6 vac

| Treatment | Basal | Pre-challenge | Sacrifice |
|---|---|---|---|
| Negative control | 0 | 0 | 0 |
| E5A (pNDV-LS(wt)/Orf5/6 vac live), 2 doses |  | 100 (1:146) | 100 (1:272) |
| E5B (pNDV-LS(wt)/Orf5/6 vac live + adjuvant), 2 doses | 0 | 100 (1:162) | 100 (1:182) |
| E5C (pNDV-LS(wt)/Orf5/6 vac inactivated + adjuvant), 2 doses | 0 | 100 (1:514) | 100 (1:58) |
| Ingelvac PRRS MLV | 0 | 0 | 0 |
| Positive control | 0 | 0 | 0 |

As can be seen, at the start of the test the SPF pigs were completely negative to the pNDV-LS(wt)Orf5/6vac vaccine in its different embodiments (E5A-E5C). However, at the time of the pre-challenge a complete seroconversion was found in the groups vaccinated with the vaccines of the present invention, being the 100% of the vaccinated animals seropositive with different antibodies titers according to the treatment used, while the negative control, the positive control and the immunized with the commercial vaccine groups remained seronegative. At the time of the sacrifice the same trend was seen, namely, the groups vaccinated with pNDV-LS(wt)Orf5/6vac kept the 100% of seroconversion in 100% of the animals and the rest of the groups remained negative.

The above shows the efficacy of the selection of a viral vector capable of generating a cellular immune response due to an increased interferon alpha and/or gamma production and capable of a quick replication, as a solution to create an effective vaccine.

Growth Performance

With the purpose of proving the development reached, the pigs were individually weighted at the start, during, and at the end of the study in the post-mortem. As can be seen in FIG. 1, there was a slight increase in the weight gain (w) of the pigs when using the vaccine of Example 5C (pNDV-LS(wt)Orf5/6vac inactivated with adjuvant), compared to the commercial vaccine.

Figure 2:
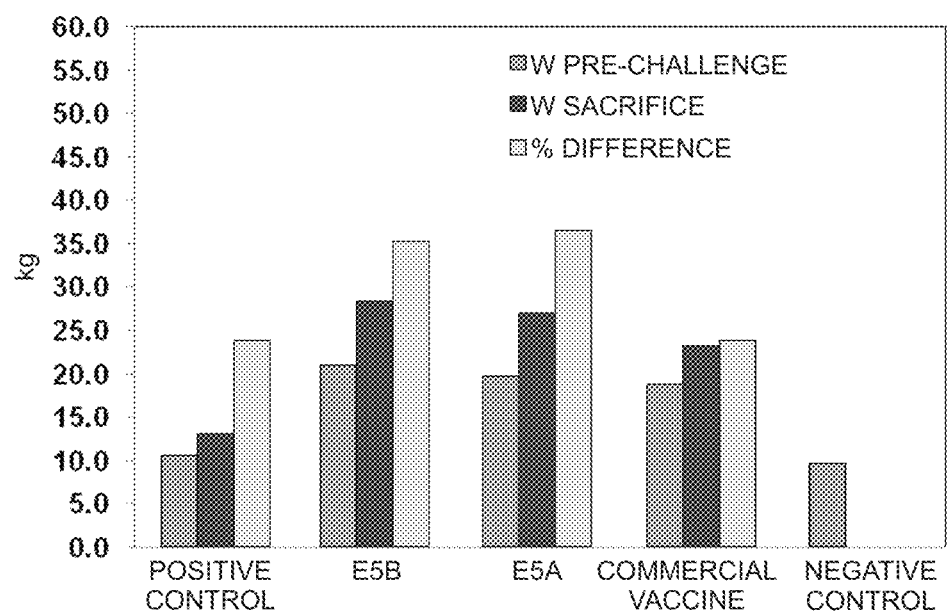
FIG. 2 shows the body weight gain in immunized pigs with the live vaccines against PRRS of the present invention, compared to the commercial vaccine.

On the other hand, regarding the pigs immunized with live vaccines (FIG. 2), it is seen that the weight gain of the animals vaccinated with pNDV-LS(wt)Orf5/6vac, with and without adjuvant, is considerably higher in comparison with the commercial vaccine.

These experiments confirm the success of the present invention, since it has been demonstrated that the vaccines of the present invention showed a clear superiority in the time to seroconvert with respect to the commercial vaccine, thereby achieving a better protection level, observed in the significant decrease of lung lesions in the pigs. With this, an improvement in the productive parameters was achieved compared to the non-vaccinated animals. Likewise, a measurable serological response different to that produced by the field pathogen virus or the existing commercial active vaccine is induced, which means that the recombinant vaccines of the present invention meets the parameter of being DIVA (Differentiation of infected from vaccinated Animals).

Although specific embodiments of the invention have been illustrated and described, emphasis must be made in that many possible modifications thereto are possible, as may be the virus used as viral vector, and the type of emulsion or vehicle used. Therefore, the present invention shall not be considered as restricted except by the prior art and by the appended claims.

The invention claimed is:

1. A viral vector capable of generating a cellular immune response in pigs, wherein the viral vector is a Newcastle disease virus comprising ORF 5 and ORF 6 of Porcine Reproductive and Respiratory Syndrome (PRRS) virus, and wherein ORF 5 has the sequence of SEQ ID NO:1 and ORF 6 has the sequence of SEQ ID NO:2.

2. A viral vector according to claim 1, wherein the Newcastle disease virus is selected from LaSota, B1, QV4, Ulster, Roakin and Komarov strains.

3. A vaccine against PRRS, comprising a Newcastle disease virus vector comprising ORF 5 and ORF 6 of PRRS virus, and a pharmaceutically acceptable vehicle, adjuvant and/or excipient, wherein ORF 5 has the sequence of SEQ ID NO:1 and ORF 6 has the sequence of SEQ ID NO:2.

4. A vaccine according to claim 3, wherein the Newcastle disease virus is live or inactivated.

5. A vaccine according to claim 3, wherein the Newcastle disease virus is selected from LaSota, B1, QV4, Ulster, Roakin and Komarov strains.

6. A vaccine according to claim 3, wherein the pharmaceutically acceptable vehicles are aqueous solutions or emulsions.

7. A vaccine according to claim 6, wherein the pharmaceutically acceptable vehicle is selected from a water-oil, oil-water, or water-oil-water emulsion.

8. A vaccine according to claim 7, wherein the pharmaceutically acceptable vehicle is a water-oil-water emulsion.

9. A vaccine according to claim 3, wherein the virus concentration required to achieve the antigenic response is between $10^{6.0}$ and $10^{10.0}$ Embryo Infectious Dose (EID) 50%/mL.

10. A vaccine according to claim 9, wherein the virus concentration required to achieve the antigenic response is between $10^{8.0}$ and $10^{9.5}$ EID 50%/mL.

11. A vaccination method to control Porcine Reproductive and Respiratory Syndrome (PRRS) comprising administering an immunologically effective amount of a vaccine against PRRS to an animal, wherein the vaccine comprises a Newcastle disease virus vector comprising ORF 5 and ORF 6 of PRRS virus, and a pharmaceutically acceptable vehicle, adjuvant and/or excipient, and wherein ORF 5 has the sequence of SEQ ID NO:1 and ORF 6 has the sequence of SEQ ID NO:2.

12. The vaccination method according to claim 11, wherein the immunized animal presents less than 12% of lung lesions after the application of two doses of the vaccine.

13. The vaccination method according to claim 11, wherein the vaccine is administered by intramuscular route, intra-nasal route, subcutaneous route, aspersion, spraying, or in drinking water.

14. The vaccination method according to claim 13, wherein the vaccine is administered by intramuscular route.

\* \* \* \* \*

SEQUENCE LISTING

<160> NUMBER OF SEQ ID NOS: 2

<210> SEQ ID NO 1
<211> LENGTH: 600
<212> TYPE: DNA
<213> ORGANISM: Porcine Reproductive and Respiratory Syndrome Virus

<400> SEQUENCE: 1

```
atgttggaga aatgcttgac cgcgggctgt tgctcgcgat tgctttcttt gtggtgtatc      60
gtgccgttct gttttgctgt gctcgccaac gccagcaacg acagcagctc ccatctacag     120
ctgatttaca acttgacgct atgtgagctg aatggcacag attggctagc taacaaattt     180
gattgggcag tggagagttt tgtcatcttt cccgttttga ctcacattgt ctcctatggt     240
gccctcacta ccagccattt ccttgacaca gtcgctttag tcactgtgtc taccgccggg     300
tttgttcacg gcggtatgt cctaagtagc atctacgcgg tctgtgccct ggctgcgttg     360
acttgcttcg tcattaggtt tgcaaagaat tgcatgtcct ggcgctacgc gtgtaccaga     420
tataccaact ttcttctgga cactaagggc agactctatc gttggcggtc gcctgtcatc     480
atagagaaaa ggggcaaagt tgaggtcgaa ggtcatctga tcgacctcaa aagagttgtg     540
cttgatggtt ccgtggcaac ccctataacc agagtttcag cggaacaatg gggtcgtcct     600
```

<210> SEQ ID NO 2
<211> LENGTH: 528
<212> TYPE: DNA
<213> ORGANISM: Porcine Reproductive and Respiratory Syndrome Virus

<400> SEQUENCE: 2

```
accatggggt cgtccttaga tgacttctgt catgatagca cggctccaca aaaggtgctt      60
ttggcgtttt ctattaccta cacgccagtg atgatatatg ccctaaaggt gagtcgcggc     120
cgactgctag ggcttctgca cctttttgatc ttcctgaatt gtgctttcac cttcgggtac     180
atgactttcg cgcactttca gagtacaaat aaggtcgcgc tcactatggg agcagtagtt     240
gcactccttt gggggtgta ctcagccata gaaacctgga aattcatcac ctccagatgc     300
cgtttgtgct tgctaggccg caagtacatt ctggcccctg cccaccacgt tgaaagtgcc     360
gcacggtttc atccgattgc ggcaaatgat aaccacgcat ttgtcgtccg gcgtcccggc     420
tccactacgg tcaacggcac attggtgccc gggttaaaaa gcctcgtgtt gggtggcaga     480
aaagctgtta aacagggagt ggtaaacctt gtcaaatatg ccaaataa                   528
```